US012599661B2

(12) United States Patent
Cherng et al.

(10) Patent No.: US 12,599,661 B2
(45) Date of Patent: Apr. 14, 2026

(54) IMMUNOGENIC COMPOSITIONS OF HEPATITIS C VIRUS AND USES THEREOF

(71) Applicant: Jaw-Ming Cherng, Yilan County (TW)

(72) Inventors: Jaw-Ming Cherng, Yilan County (TW); Jonathan Cherng, Cambridge (CA)

(73) Assignee: Jaw-Ming Cherng, Yilan County (TW)

( * ) Notice: Subject to any disclaimer, the term of this patent is extended or adjusted under 35 U.S.C. 154(b) by 722 days.

(21) Appl. No.: 18/064,299

(22) Filed: Dec. 12, 2022

(65) Prior Publication Data

US 2024/0189421 A1 Jun. 13, 2024

(51) Int. Cl.
| | |
|---|---|
| *A61K 39/29* | (2006.01) |
| *A61P 31/14* | (2006.01) |
| *C12N 7/00* | (2006.01) |
| *A61K 39/00* | (2006.01) |

(52) U.S. Cl.
CPC .............. *A61K 39/29* (2013.01); *A61P 31/14* (2018.01); *C12N 7/00* (2013.01); *A61K 2039/5254* (2013.01); *A61K 2039/545* (2013.01); *C12N 2770/24234* (2013.01); *C12N 2770/24251* (2013.01); *C12N 2770/24271* (2013.01)

(58) Field of Classification Search
None
See application file for complete search history.

(56) References Cited

FOREIGN PATENT DOCUMENTS

WO WO-2004024904 A2 * 3/2004 .............. A61P 31/14

OTHER PUBLICATIONS

Vieyres et al., Viruses, Mar. 2014, 6(3):1149-1187 (Year: 2014).*
Venetz et al., PNAS 2015, 112(7):2000-2005 (Year: 2015).*

* cited by examiner

*Primary Examiner* — Stacy B Chen
(74) *Attorney, Agent, or Firm* — Hannah Tien

(57) ABSTRACT

A method for preparing an immunogenic composition, which comprises treating HCV pseudoparticles with α2-3, 6,8,9 neuraminidase A to generate the immunogenic composition. In addition, the immunogenic compositions are made in vaccines for eliciting an immune response to HCV in a subject.

4 Claims, 4 Drawing Sheets
(1 of 4 Drawing Sheet(s) Filed in Color)
Specification includes a Sequence Listing.

IMMUNOGENIC COMPOSITIONS OF HEPATITIS C VIRUS AND USES THEREOF

This application contains a Sequence Listing in a computer readable form, the file name is 4009-CJM-SEQList, created on Dec. 6, 2022, the size is 4 KB, which is incorporated herein by reference.

FIELD OF THE INVENTION

The present invention provides immunogenic compositions comprising hepatitis C virus (HCV) pseudoparticles treated with α2-3,6,8,9 neuraminidase A. In addition, the present invention further provides methods of eliciting an immune response to HCV in a subject by administration of the immunogenic compositions.

DESCRIPTION OF PRIOR ART

Hepatitis C virus (HCV) is a major causative agent of chronic liver disease affecting approximately 170 million people worldwide. The majority (~85%) of individuals infected by HCV become chronically infected and are at risk of developing cirrhosis and hepatocellular carcinoma. HCV, a member of the Flaviridae, is an enveloped virus containing a positive strand genomic RNA. Based on genome sequence similarity, HCV is grouped into six major genotypes and numerous subtypes. The HCV RNA genome contains a single open reading frame flanked by untranslated regions (UTRs) at both the 5' and 3' ends. The positive strand genomic RNA encodes a single polyprotein of approximately 3010 amino acids that is processed co- and post-translationally by host and viral proteases into structural proteins (C, E1, E2, and p7) and nonstructural proteins (NS2, NS3, NS4A, NS4B, NS5A and NS5B).

Viral attachment and entry, which represents the first interaction of the virus with the host cell, are major targets of adaptive humoral responses. The viral proteins responsible for cell attachment and entry of HCV are the glycoproteins E1 and E2. Viral proteins are recognized as nonself by the host's immune system and induce the production of antibodies. A small proportion of these antibodies exhibits antiviral activity in vitro and is defined as virus-neutralizing antibodies. Neutralizing antibody responses often provide a first-line adaptive defense against infection by limiting virus spread. Thus, the expression of these glycoproteins has important application in vaccine discovery and drug targeting. Knowledge of genotypic and quasispecies variation on viral glycoprotein properties is important in understanding the structure-function relationship of the proteins.

The envelope glycoproteins E1 and E2 are the natural targets for neutralizing antibodies. The E2 is a preferred target for humoral and cell-mediated immune responses. Not surprisingly, a large share of HCV sequence variation is concentrated within the hypervariable regions of E2. These regions are known to exhibit a high degree of variability and are used to distinguish between HCV isolates of the same subtype and for determination of quasispecies (the coexistence of different sequences in the same patient).

Glycans associated with viral envelopes play a major role in masking neutralization epitopes and modulating the overall immunogenicity of viral particles. Virus proteins are usually glycosylated via one of three different mechanisms. These processes not only differ in cellular enzymes that are involved, but they also give rise to different types of glycan structure. The resulting glycans are referred to as being either N-linked, O-linked, or glycosylphosphatidyl inositol (GPI)-anchored. In the process of N-linked glycosylation, the glycan chains are added to the virus protein via an asparagine residue. N-linked glycosylation occurs at sites within the protein where the consensus amino acid sequence Asn-X-Ser/Thr is present. This is by far the most common way in which virus proteins are glycosylated, and the process by which they undergo N-linked glycosylation is similar to that which occurs on cellular glycoproteins.

Most of the glycosylation sites on HCV envelope glycoproteins are conserved, and some of the glycans associated with these proteins have been shown to play an essential role in protein folding and HCV entry. Such a high level of glycosylation suggests that these glycans can limit the immunogenicity of HCV envelope proteins and restrict the binding of some antibodies to their epitopes on the virion surface, as observed for human immunodeficiency virus (HIV) gp120. It is reported that at least three glycans on E2 (E2N1, E2N6, and E2N11) reduce the sensitivity of HCVpp to antibody neutralization and these glycans also reduced the access of CD81 to its E2 binding site. In contrast, no evidence shows that N-linked glycans of E1 contribute to the masking of neutralizing epitopes. These data suggest that glucans E2N1, E2N6, and E2N11 are close to the binding site of CD81 and modulate both CD81 and neutralizing antibody binding to E2. In short, this work indicates that this region is a major target of neutralizing antibodies and HCV glycans contribute to the evasion of HCV from the humoral immune response.

The discovery of anti-HCV compounds and the development of HCV vaccines have been severely hampered by the lack of cell culture replication systems. Since the late 1990s, the advent of subgenomic replicons that model the intracellular events leading to HCV genome replication have enabled the discovery of HCV protease and polymerase inhibitors, but did not allow the study of HCV entry or entry inhibitors. More recently, the function of HCV E1E2 in cell attachment and entry has been investigated using the retrovirus-based pseudoparticle (pp) assay (that recapitulates the entire HCV replication cycle were achieved) whereby infectivity of the retroviral particles is conferred by HCV E1E2 envelope proteins. These new experimental systems have enabled a rapid advance in knowledge of how HCV glycoproteins, E1 and E2, mediate receptor binding and viral entry. These systems have facilitated the discovery of a range of viral receptors. This $HCV_{pp}$ assay has been particularly useful in the functional analysis of HCV E1E2 derived from patients infected with diverse genotypes and subtypes of the virus, in dissecting the role in virus entry of key E2 receptors, CD81 and SR-B1, and in measuring the capacity of antibodies and patient sera to neutralize infection of target cells by $HCV_{pp}$.

Recently, infectious pseudotype particles that are assembled by displaying unmodified HCV envelope glycoproteins on retroviral core particles have been successfully generated. HCV pseudoparticles ($HCV_{pp}$) are produced by transfecting 293T cells with three expression vectors encoding the E1E2 polyprotein, the retroviral core proteins and a packaging-competent retrovirus-derived genome containing a marker gene. Surprisingly, in the absence of any modification of HCV envelope glycoproteins, infectious pseudoparticles were produced. The data that have been accumulated on these pseudotype particles strongly suggest that they mimic the early steps of HCV infection. Indeed, they exhibit a preferential tropism for hepatic cells, and they are specifically neutralized by anti-E2 monoclonal antibodies as well as sera of HCV-infected patients. Therefore, the $HCV_{pp}$ represent the best tool currently available to study functional HCV envelope glycoproteins and provide a model system to study HCV cell entry. The development of $HCV_{pp}$ offers the possibility to study HCV neutralization with defined sequences of HCV envelope glycoproteins, and the use of $HCV_{pp}$ in neutralization studies has been validated. It has been shown that a progressive emergence of a relatively strong neutralizing response to be in correlation with a decrease in viremia.

SUMMARY

The present invention provides a method for preparing an immunogenic composition, which comprises treating HCV pseudoparticles with α2-3,6,8,9 neuraminidase A to generate the immunogenic composition. The present invention also provides immunogenic compositions comprising HCV pseudoparticles treated with α2-3,6,8,9 neuraminidase A. In addition, the present invention further provides methods of eliciting an immune response to HCV in a subject by administration of the immunogenic compositions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
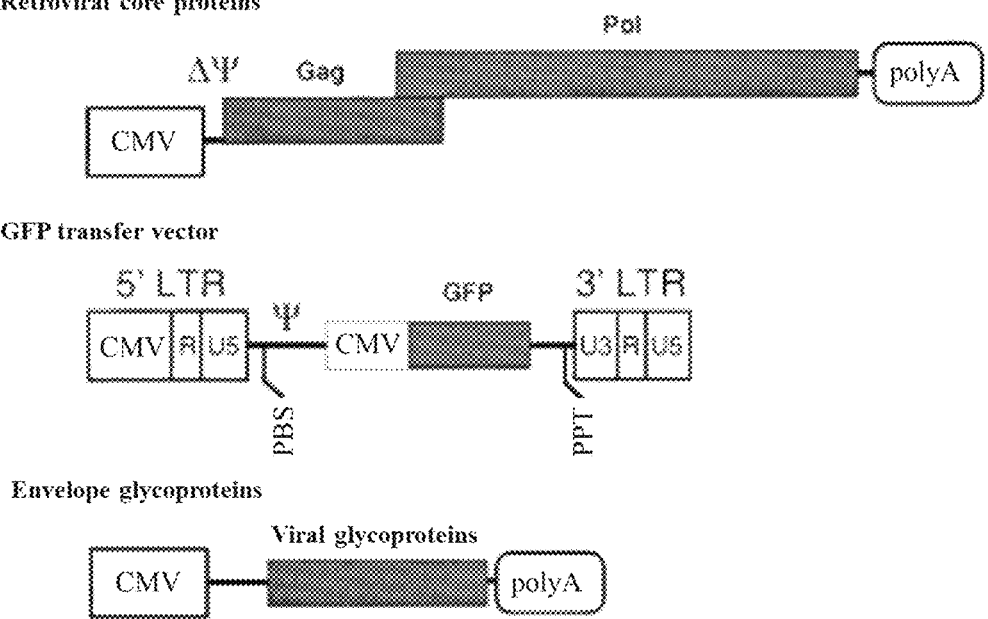
FIG. 1 shows transfer vector constructs for producing HCV pseudoparticles.

Viral attachment and entry, which represents the first interaction of the virus with the host cell, are major targets of adaptive humoral responses. The viral proteins responsible for cell attachment and entry of HCV are the glycoproteins E1 and E2. The present invention proposes that deglycosylation of E1 and E2 by glycosidase, such as α2-3,6,8,9 neuraminidase A (a broad specificity glycosidase, which cleaves linear and branched non-reducing terminal sialic acid residues from glycoproteins, glycopeptides, and oligosaccharides) may enhance not only the sensitivity of detection of neutralizing antibody activity but also elicit an immune response that recognizes E1 and E2 variants in higher titer. To investigate the immunogenicity and protective capacity of the HCV pseudoparticles treated with α2-3, 6,8,9 Neuraminidase A, the mouse model is used. In this present invention, the abilities of anti-sera from $HCV_{Neura-A}$-immunized mice to inhibit entry of $HCV_{pp}$ into Huh7.5 cells (represented by suppression of infection rate of Huh7.5 cells by $HCV_{pp}$) were tested. This present invention shows that, compared to the control, immunization with $HCV_{Neura-A}$ induces effective systematic humoral responses with neutralizing activity resulting in effectively inhibiting the infection rate of Huh7.5 cells by $HCV_{pp}$. This present invention indicates that the anti-sera from $HCV_{Neura-A}$-immunized mice can effectively neutralize $HCV_{pp}$, resulting in suppressing $HCV_{pp}$ (bearing the parental intact and unmodified envelope glycoprotein) from entering the cell and thereby, suppressing the infection of Huh7.5 cells by $HCV_{pp}$. Thus, based on the results obtained from the above neutralization studies, an effective vaccine against HCV infection can be designed using deglycosylation of $HCV_{pp}$.

This strategy (Hydrolysis of sialic acid residues from glycoproteins on $HCV_{pp}$ by α2-3,6,8,9 neuraminidase A) of the present invention opens a new direction for vaccine design and, together with other different vaccine strategies, should facilitate the development of vaccines against HCV.

The terms "a" or "an" herein are used to describe the elements and components of the present invention. This term is used only for convenience of description and to give a basic idea of the present invention. This description should be understood to include one or at least one, and unless it is clear that it is indicated otherwise, the singular also includes the plural. When used in conjunction with the word "comprising" in a claim, the term "a" may mean one or more than one.

The term "or" as used herein in a claim means "and/or," unless expressly indicated to mean only the other option, or unless the other options are mutually exclusive.

The present invention provides a method for preparing an immunogenic composition comprising a viral antigen of hepatitis C virus (HCV), the method comprising: (a) providing HCV pseudoparticles; (b) treating the HCV pseudoparticles with α2-3,6,8,9 neuraminidase A to remove sialic acids on the surfaces of the HCV pseudoparticles; and (c) isolating the HCV pseudoparticles produced in step (b) to generate the immunogenic composition.

In the present invention, the preparing method of the HCV pseudoparticles comprises: (1) delivering expression constructs into cells, wherein the expression constructs comprise sequences for encoding glycoproteins E1 and E2 of HCV, retroviral core proteins and retrovirus-derived genome; and (2) isolating the HCV pseudoparticles produced by the cells.

In one embodiment, the sequence for encoding glycoproteins E1 and E2 of HCV comprises the sequence of SEQ ID No: 1.

In this preparing method of the HCV pseudoparticles, it is possible to design three independent expression constructs that contain the three nucleic acid sequences for encoding retroviral core, genome and hepacivirus glycoproteins, or, alternatively, it is also possible to design an expression construct that contains the different nucleic acid sequences. Such expression constructs are delivered into the cells, thereby inducing the production of further replicating hepacivirus-pseudo-particles. In this case, the genome of a retrovirus is modified so as to express the hepacivirus glycoproteins E1 and E2 in place of the retroviral Env gene (encoding the retroviral glycoproteins). The genes encoding the retroviral core proteins are left unchanged. Furthermore, an additional gene, encoding a marker gene or an immuno-modulator, for example, can be expressed from this genome.

In one embodiment, the cells are in vitro cells. In a preferred embodiment, the cells comprise mammalian cells. In a more preferred embodiment, the cells comprise human embryonic kidney cells.

In the present invention, the delivering of the expression constructs may be performed by any standard method well known by one skilled in the art, e.g. transfection, electroporation, microinjection, transduction, cell fusion, DEAE dextran, calcium phosphate precipitation, or use of a gene gun.

In one embodiment, the expression constructs further comprise a sequence for encoding a marker gene. In a preferred embodiment, the marker gene is green fluorescent protein (GFP). The purpose of the marker gene is used for screening successfully transfected cells.

The term "hepatitis C virus" ("HCV"), as used herein, refers to any one of a number of different genotypes and isolates of hepatitis C virus. Thus, "HCV" encompasses any of a number of genotypes, subtypes, or quasispecies, of HCV, including, e.g., genotype 1, 2, 3, 4, 6, 7, etc. and subtypes (e.g., 1a, 1b, 2a, 2b, 3a, 4a, 4c, etc.), and quasispecies. Representative HCV genotypes and isolates include: the "Chiron" isolate HCV-1, H77, J6, Con1, isolate 1, BK, EC1, EC10, HC-J2, HC-J5; HC-J6, HC-J7, HC-J8, HC-JT, HCT18, HCT27, HCV-476, HCV-KF, "Hunan", "Japanese", "Taiwan", TH, type 1, type 1a, H77 type 1b, type 1c, type 1d, type 1e, type 1f, type 10, type 2, type 2a, type 2b, type 2c, type 2d, type 2f, type 3, type 3a, type 3b, type 3g, type 4, type 4a, type 4c, type 4d, type 4f, type 4h, type 4k, type 5, type 5a, type 6 and type 6a.

The HCV genome encodes two membrane-associated envelope glycoproteins (E1 and E2), which interact to form a noncovalent heterodimeric complex. HCV glycoproteins, E1 and E2, are heavily modified by N-linked glycosylation. The E1 protein consists of 192 amino acids and contains 5 to 6 N-glycosylation sites, depending on the HCV genotype. The E2 protein consists of 363 to 370 amino acids and contains 9-11 N-glycosylation sites, depending on the HCV genotype.

In one embodiment, the viral antigen of HCV comprises glycoproteins E1 and E2 of HCV. The glycoproteins E1 and E2 of HCV are expressed on the surfaces of the HCV pseudoparticles. In a preferred embodiment, the HCV pseudoparticles have glycoproteins E1 and E2 of HCV.

As used herein, $\alpha$2-3,6,8,9 neuraminidase A is a broad specificity sialidase, which cleaves linear and branched non-reducing terminal sialic acid residues from glycoproteins, glycopeptides, and oligosaccharides. Therefore, the present invention removes the sialic acid from the glycoproteins E1 and E2 on the HCV pseudoparticles by $\alpha$2-3,6,8,9 neuraminidase A to elicit the immunogenicity of the HCV pseudoparticles.

In another embodiment, the HCV pseudoparticles are treated with $\alpha$2-3,6,8,9 neuraminidase A for 0.5 to 4 hr in the step (b). In a preferred embodiment, the HCV pseudoparticles are treated with $\alpha$2-3,6,8,9 neuraminidase A for 0.5 to 3 hr in the step (b). In a more preferred embodiment, the HCV pseudoparticles are treated with $\alpha$2-3,6,8,9 neuraminidase A for 1 to 2 hr in the step (b).

In one embodiment, the method further comprises a step (d), comprising mixing the HCV pseudoparticles of the step (c) with a pharmaceutically acceptable carrier to generate the immunogenic composition. Furthermore, the HCV pseudoparticles of the step (c) can combine with the pharmaceutically acceptable carrier to generate a HCV vaccine.

The present invention also provides an immunogenic composition for eliciting an immune response to hepatitis C virus (HCV), wherein the immunogenic composition comprising HCV pseudoparticles treated with $\alpha$2-3,6,8,9 neuraminidase A.

In addition, the immunogenic composition optionally along with a suitable pharmaceutically acceptable carrier will optimize the protective effects of a HCV vaccine. In one embodiment, the HCV vaccine comprises the immunogenic composition and a pharmaceutically acceptable carrier.

The present invention further provides a method of inducing an immune response in a subject to a hepatitis C virus (HCV), which comprises administering to the subject an effective amount of a HCV vaccine, wherein the HCV vaccine comprises an immunogenic composition, and the immunogenic composition comprises HCV pseudoparticles treated with $\alpha$2-3,6,8,9 neuraminidase A.

In one embodiment, the subject is an animal, preferably a mammal, more preferably a human.

The present invention also provides a use of an immunogenic composition for preparing a HCV vaccine, wherein the immunogenic composition comprises HCV pseudoparticles treated with $\alpha$2-3,6,8,9 neuraminidase A.

The vaccines of the present invention can be included in a pharmaceutical or nutraceutical composition or formulation together with additional active agents, carriers, vehicles, adjuvants, excipients, or auxiliary agents identifiable by a person skilled in the art upon reading of the present invention.

Suitable adjuvants for inclusion in compositions of the present disclosure include those that are well known in the art, such as complete Freund's adjuvant (CFA) that is not used in humans, incomplete Freund's adjuvant (IFA), squalene, squalane, alum, and various oils, all of which are well known in the art, and are available commercially from several sources, such as Novartis (e.g., MF59 adjuvant).

In another embodiment, the vaccine comprises a pharmaceutically acceptable carrier. Thus, the immunogenic composition or the vaccine in the present invention further comprises the pharmaceutically acceptable carrier.

As used herein, the term "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the vaccine. The vaccine is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzylalcohol or methyl parabens; antioxidants such as ascorbic acid or sodium bisulfite; chelating agents such as ethylenediamine tetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

For parenteral administration, the immunogenic composition of the present invention or vaccines therefrom may be administered by intravenous, subcutaneous, intramuscular, intraperitoneal, or intradermal injection, alone or in compositions further comprising pharmaceutically accepted carriers. For administration by injection, it is preferred to use the immunogenic composition in a solution in a sterile aqueous vehicle which may also contain other solutes such as buffers or preservatives as well as sufficient quantities of pharmaceutically acceptable salts or of glucose to make the solution isotonic. The immunogenic composition of the present invention can be obtained in the form of therapeutically acceptable salts that are well-known in the art.

The vaccines may also be administered orally. Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such ascolloidal silicon dioxide; a sweetening agent such as sucrose or saccharin; or a flavoring agent such as peppermint, methyl salicylate, or orange flavoring.

Systemic administration can also be transmucosal or transdermal. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration may be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

It will be further appreciated that the amount of the immunogenic composition or the vaccine of the present invention that is useful in treatment or prevention of HCV will vary with the route of administration, the nature of the condition being treated, and the age and condition of the subject, and will ultimately be at the discretion of the attendant physician.

The concentration of immunogen for inclusion in the vaccine is an amount which induces an immune response without significant, adverse side effects. Such amount will vary depending on which immunogen is used and the type and amount of adjuvant included in the vaccine. Typically, a vaccine will comprise immunogen in an amount of from about 0.1 to about 1000 µg per ml, more preferably from about 0.2 to about 100 µg per ml and most preferably about 0.5 µg to about 10 µg per ml. Following an initial vaccination, subjects being vaccinated may receive one or several booster immunizations adequately spaced thereafter.

It will be appreciated by those skilled in the art that reference herein to treatment extends to prophylaxis as well as the treatment of established infections or symptoms. The immunogenic composition and vaccines of the present invention may be administered therapeutically or prophylactically. Treatment is preferably commenced before or at the time of infection or at the time the mammal is exposed to HCV infection, and continued until virus is no longer present. However, the treatment can also be commenced post-infection, after the mammal has been exposed to HCV infection, or after the appearance of established symptoms of infection.

Thus, the immunogenic composition of the present invention, when administered to a subject in need thereof, induces an immune response (e.g., a cellular immune response) in the subject to one or more HCV genotypes.

EXAMPLES

The present invention may be embodied in many different forms and should not be construed as limited to the examples set forth herein. The described examples are not intended to limit the scope of the invention as set forth in the claims.

Materials and Methods

I. Reagents $\alpha$2-3,6,8,9 Neuraminidase A (Neura-A) was purchased from New England Biolabs (Ipswich, MA, USA). DMEM, fetal bovine serum, streptomycin, and penicillin were purchased from GIBCO BRL (Gaithersburg, Md, USA). Freund's Complete/Incomplete Adjuvants were purchased from Sigma Aldrich, Inc. (St. Louis, Mo, USA). Mag4C LV kit was purchased from OZ Biosciences (Av. de Luminy, Marseille, France). Macrosep Advance Centrifugal Device, MWCO 100K, was purchased from Pall Corporation (Port Washington, New York, USA). TransIT-LT1 Transfection Reagent was purchased from Mirus, Inc. (Madison, WI, USA).

II. Cells Culture

HEK293T and Huh7.5 cells were cultured in DMEM medium (Gibco), supplemented with 10% (v/v) fetal bovine serum, 10 U/mL penicillin, 10 µg/mL streptomycin, and 0.25 µg/mL amphotericin B at 37° C. with 5% $CO_2$.

III. Production of HCV Pseudoparticles ($HCV_{pp}$)

E1E2 and retroviral expression constructs (FIG. 1) used for the production of HCV pseudoparticles ($HCV_{pp}$) were kindly provided by Dr. B. Bartosh and Dr. F. L. Cosset (INSERM U758, Lyon, France). $HCV_{pp}$ was prepared as described below (including HCV E1E2 expression, packaging, and transfer vectors).

III.1. Packaging of the Transfer Vector Constructs

FIG. 1 showed the CMV-Gag-Pol murine leukemia virus (MLV) packaging construct, encoding the MLV gag and pol genes, and the MLV-GFP plasmid, encoding the MLV-based transfer vector containing a CMV-GFP internal transcriptional unit. This system exploited two well-documented properties of retroviruses, the capacity to incorporate foreign glycoproteins and the capacity to integrate and express marker genes from replication-incompetent viral particles, which generated a specific, fast, and reliable in vitro infection assay based on pseudoparticles displaying unmodified E1 and E2 HCV glycoproteins. HCV pseudoparticles ($HCV_{pp}$) were generated by assembling these full-length, unmodified E1 and E2 glycoproteins onto retroviral core proteins derived from MLV. Retroviruses were chosen as platforms for assembly of HCVpp because their cores could incorporate a variety of different cellular and viral glycoproteins, and because they could easily package and integrate genetic markers into DNA of infected cells. Analysis of immunoblots of transfected cells showed that the structural components of the pseudoparticles were readily detected at the expected molecular masses; i.e., ~30 kD for E1, ~60 kD for E2, ~60 kD for VSV-G. Thus, this system describes for the first time the formation of highly infectious HCV pseudoparticles that may share early cell entry properties with parental HCV.

III.2. Preparation and Purification of Plasmids

The plasmids phCMV-cE1E2(1a), CMV-Gag-Pol MLV, and CMV-GFP MLV were propagated in *E. coli*, isolated, and purified by equilibrium centrifugation in CsCl-ethidium bromide gradient (to be used for the production of HCVpp by transfecting into HEK293T cells).

III.3. Production of Native Fully Glycosylated Pseudoparticles (HCV$_{pp}$)

To generate HCV$_{pp}$ with native fully glycosylated E1E2, human embryonic kidney (HEK293T) cells were transfected with expression vectors encoding the viral components, i.e., E1E2 glycoproteins (phCMV-cE1E2(1a)), retroviral core proteins (CMV-Gag-Pol MLV), and packaging-competent GFP-containing retroviral transfer vectors (CMV-GFP MLV). The sequences encoding the E1 and E2 glycoproteins from a 1a-type HCV published by these researchers on GenBank (GenBank accession number AY734972.1) are SEQ ID NO: 1. Therefore, the present invention added the sequence of SEQ ID No: 1 into the expression vectors for expressing glycoproteins E1 and E2.

In brief, the Gag-Pol packaging construct (12 μg), the transfer vector construct (12 μg), and the glycoprotein-expressing construct (4 μg) DNAs were transfected into $2.5 \times 10^6$ HEK293T cells seeded the day before in 10-cm plates using TransIT-LT1 transfection reagent fromMirus, Inc. (Madison, WI, USA) according to the manufacturer's protocol. The medium (8 mL/plate) was replaced 16 h after transfection. Supernatants containing the pseudoparticles were harvested 48 h after transfection, filtered through 0.45 μm pore-sized membranes (to be used for infecting Huh7.5 cells) and concentrated 20 fold using Macrosep Advance Centrifugal Device, MWCO 100K.

IV. Generation of the test vaccines (HCV$_{pp}$ & HCV$_{Neura-A}$)

For the test vaccine HCV$_{Neura-A}$, native fully glycosylated HCVpp was cleaved using α2-3,6,8,9 Neuraminidase A (FIG. 4) to produce HCV$_{Neura-A}$ as described below: (1) Combined 10 μg of HCVpp and H$_2$O in a total reaction volume of 90 μL; (2) Added 10 μL of GlycoBuffer 1 (10×) to make a 100 μL total reaction volume; (3) Added 10 μL of α2-3,6,8,9 Neuraminidase A; and (4) Incubated at 37° C. for 1 hour.

For control experiment using native fully glycosylated HCVpp as vaccine, HCVpp was proceeded in the same way described above without adding α2-3,6,8,9 Neuraminidase A.

Finally, the products were purified by Mag4C LV magnetic nanoparticlekit from OZ Biosciences according to manufacturer's protocol.

V. Immunogenicity of the Test Vaccines (HCV$_{pp}$ & HCV$_{Neura-A}$)

It was known that glycosylation affects protein folding as well as protein function. Glycans associated with viral envelopes also played a major role in masking neutralization epitopes and modulated the overall immunogenicity of viral particles. Such a high level of glycosylation on E1E2 suggested that these glycans can limit the immunogenicity of HCV envelope proteins and restricted the binding of some antibodies to their epitopes on the virion surface, as observed for human immunodeficiency virus (HIV) gp120.

Furthermore, previous study with influenza demonstrated that monoglycosylated hemagglutinin showed similar secondary structure and better binding affinity to host receptors compared with its fully glycosylated counterpart. In addition, a single GlcNAc residue to Asn is the minimum component of the N-glycan required for glycoprotein folding and stabilization.

To investigate the effect of deglycosylation on HCV$_{pp}$ using α2-3,6,8,9 Neuraminidase A, BALB/c mice were immunized with normal saline (used as control), HCV$_{pp}$, or HCV$_{Neura-A}$.

V.1. In Vivo Animal Study

Female BALB/c, 6-8 weeks old, were purchased from BioLASCO (BioLASCO, Taipei, Taiwan) and maintained in conditions in accordance with relevant guidelines and regulations for the care and use of laboratory animals of China Medical University.

Thirty mice were randomly and equally divided into 3 groups for evaluation of immunogenicity and toxicity of the test vaccines HCV$_{pp}$ and HCV$_{Neura-A}$.

Antisera were raised in mice by injection each of 5 μg of HCV$_{pp}$ HCV$_{Neura-A}$, or normal saline (for the control group) with equal volume of Freund's adjuvants via i.p. route on day 1, 14, and 28. Antisera were obtained on day 1, 14, 28, and 42. All serum samples were stored at −80° C. upon collection.

Antisera from each group of immunization were compared and analyzed using neutralizing assay with regard to their abilities to bind native fully glycosylated HCV$_{pp}$ (suggested by infection suppressing activities).

V.2. Neutralization Assays

To evaluate the neutralization activities of sera from the immunized mice, sera of control, HCV$_{pp}$-, and HCV$_{Neura-A}$-immunized mice were used for the study.

Huh7.5 cells were pre-seeded into 12-well cell culture plates at a density of $1 \times 10^5$ per well. The next day, the HCV$_{pp}$ supernatants (225 μL/well) were incubated with equal volume of the 1:2 diluted antisera from control, HCVpp-, and HCV$_{Neura-A}$-immunized mice at 37° C. for 1 hour. The mixtures were then added to each well. After incubation at 37° C. for 3 hours, the supernatants were replaced with fresh culture medium and incubated for 72 hours at 37° C. HCV entry was determined as the percentage of GFP-positive cells measured by Countess II FL Automated Cell Counter (ThermoFisher Scientific, USA).

VI. Statistical Analysis

Data were presented as means±standard error. The evaluation of statistical significance was determined by one-way analysis of variance (ANOVA) and p values were calculated using the SPSS 16.0 software. A p value less than 0.05 was considered statistically significant.

Results

Preparation and Purification of Plasmids

Figure 2:
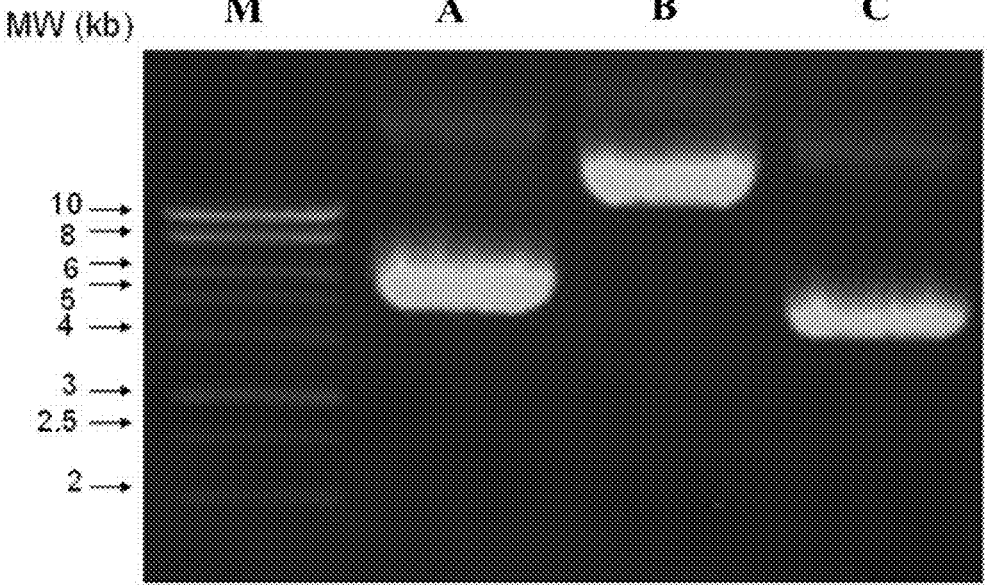
FIG. 2 shows the electrophoresis analysis in 0.7% agarose gel of the purified plasmids. Molecular weight (MW) markers (in kb) are indicated on the left. M: marker. A: phCMV-cE1E2(1a), MW=7,754 bp. B: CMV-Gag-Pol MLV, MW=11,984 bp. C: CMV-GFP MLV, MW=6,309 bp.

The plasmids phCMV-cE1E2(1a), CMV-Gag-Pol MLV, and CMV-GFP MLV were propagated in *E. coli*, isolated, and purified by equilibrium centrifugation in CsCl-ethidium bromide gradient. The purity was monitored by 0.7% agarose gel electrophoresis as shown in FIG. 2.

Production of Native Fully Glycosylated Pseudoparticles (HCV$_{pp}$)

Figure 3:
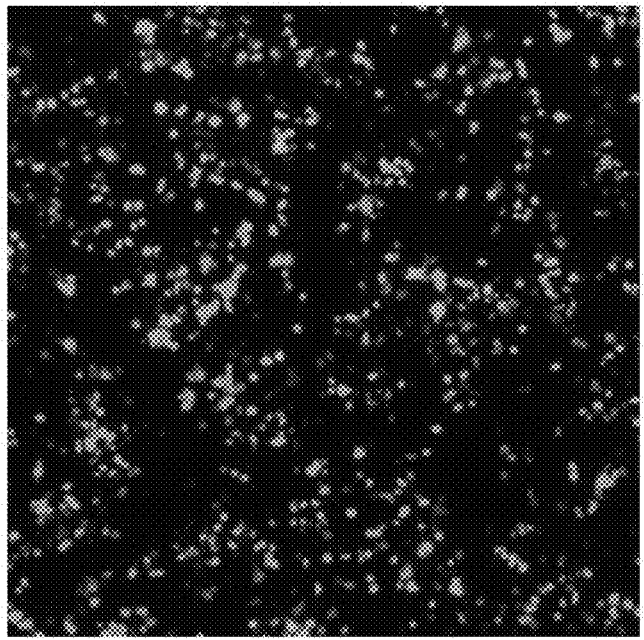
FIG. 3 shows the transfected HEK293T with strong green fluorescence.

To generate HCV$_{pp}$ with native fully glycosylated E1E2, human embryonic kidney (HEK293T) cells were transfected with expression vectors encoding the viral components, i.e., E1E2 glycoproteins, retroviral core proteins, and packaging-competent GFP-containing retroviral transfer vectors. Finally, the successfully transfected cells with strong green fluorescence were produced (FIG. 3).

Immunogenicity in Balb/c Mice: Protective Capacity of $HCV_{Neura-A}$-Immunized Mouse Sera In order to test the functionality of the test vaccines $HCV_{pp}$ & $HCV_{Neura-A}$, all samples from control, $HCV_{pp}$- and $HCV_{Neura-A}$-immunized mice were tested for their abilities to inhibit Huh7.5 cells by $HCV_{pp}$ using neutralization test.

The main correlates of potency of the test vaccines were the level of neutralizing antibody (NtAb), manifesting as infection suppressing activity in neutralization assay using Huh7.5 cells. Neutralization activities were compared between sera of saline-immunized mice and that of $HCV_{pp}$- or $HCV_{Neura-A}$-immunized mice. Toxicity of the vaccines was also evaluated.

The present invention found that, compared to the control group, all 10 serum samples from $HCV_{Neura-A}$-immunized mice inhibited the infection activities of HCVpp significantly, suggesting efficient neutralizing and protective capacities.

Figure 4:
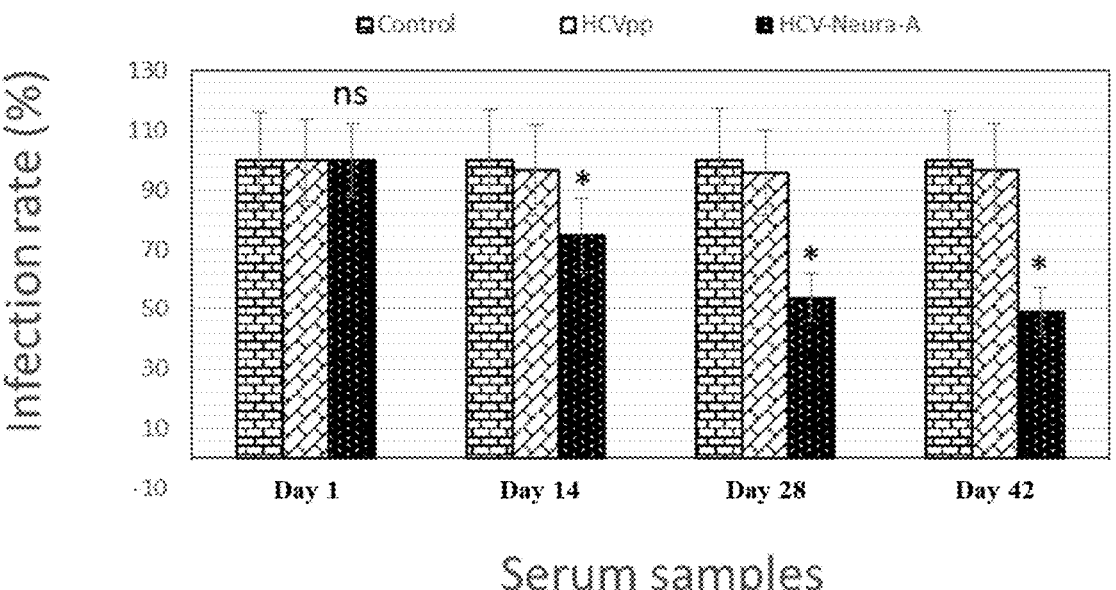
FIG. 4 shows the neutralizing capacities of $HCV_{Neura-A}$-immunized mouse sera. Compared with control (injected with normal saline) mice, sera from $HCV_{Neura-A}$-immunized mice exhibit effective neutralizing activities (suggested by infection suppressing levels). However, no significant inhibition is observed with sera from $HCV_{pp}$-immunized mice. Immunizations are performed in 6-8 weeks old, female Balb/c mice (n=10 for the control/experimental group) via i.p. route. 5 μL of normal saline (for the control group), 5 μg of $HCV_{pp}$ or $HCV_{Neura-A}$ per mouse is inoculated with Freund's adjuvant. Priming on day 1, boosting on day 14, and 28; bleeding on day 1, 14, 28, and 42. Data are expressed as means±standard error of mean, n=10. *, ns indicates p<0.05 and no significant statistical difference from the control, respectively.

With $HCV_{Neura-A}$-immunized mice, levels of suppression on infection were correlated with priming and boosting times. As shown in FIG. 4, the suppressions on infection were detected 14 days post-priming at a significant level (74.69%±12.53) compared to those of the control mice. Post-priming on day 1 and boosting on day 14, the neutralizing activities reached high levels (53.87%±7.96) on day 28 and remained at high levels (49.09±8.17) to days 42 (with second boosting on day 28), suggesting neutralizing activities (and specific protective NtAb against $HCV_{pp}$ infection) increased in the same way.

However, with the sera from native fully glycosylated $HCV_{pp}$-immunized mice, no significant of suppression on infection was observed. As shown in FIG. 4, the suppressions on infection detected 14 days post-priming was low (96.47%±15.26) compared to those of the control mice. Post-priming on day 1 and boosting on day 14, the neutralizing activities remained low levels (95.57%±14.17) on day 28, and still remained at the low levels (96.43%±15.69) to days 42 (with second boosting on day 28).

Toxicity

6-Week toxicokinetic study of the test vaccines was performed. As described above, a total of 30 mice were randomly assigned to 3 groups (10 animals/group) including the saline (control), $HCV_{pp}$, and $HCV_{Neura-A}$ groups via i.p. route, on days 1, 14, and 28.

Under the conditions of this present invention, no morbidity or mortality was noted; no abnormal reaction, body weight loss, or other obvious systemic toxicity was noted in clinical observation in all animals during the period of administration and at the end of 2-week recovery period.

Those who skilled in the art will understand the above concept as a description of the methods used to convey the deposited application information. Those one skilled in the art recognize that these are illustrative only and that many equivalents are possible.

```
Sequence Listing
<ST26SequenceListing dtdVersion="V1_3" fileName="4009_Sequence Listing.xml" softwareName="WIPO
Sequence"software Version="2.1.1" productionDate="2022-11-15">
<ApplicantFileReference>4009-CJM-US</ApplicantFileReference>
<ApplicantName languageCode="en">Jaw-Ming Cherng</ApplicantName>
<InventorName languageCode="en">Jaw-Ming Cherng</InventorName>
<InventionTitle languageCode="en">IMMUNOGENIC COMPOSITIONS OF HEPATITIS C VIRUS AND
USES THEREOF</InventionTitle>
<SequenceTotalQuantity>1</SequenceTotalQuantity>
<SequenceData sequenceIDNumber="1">
<INSDSeq>
<INSDSeq_length>1734</INSDSeq_length>
<INSDSeq_moltype>DNA</INSDSeq_moltype>
<INSDSeq_division>PAT</INSDSeq_division>
<INSDSeq_feature-table>
<INSDFeature>
<INSDFeature_key>source</INSDFeature_key>
<INSDFeature_location>1..1734</INSDFeature_location>
<INSDFeature_quals>
<INSDQualifier>
<INSDQualifier_name>mol_type</INSDQualifier_name>
<INSDQualifier_value>other DNA</INSDQualifier_value>
</INSDQualifier>
<INSDQualifier id="q2">
<INSDQualifier_name>organism</INSDQualifier_name>
<INSDQualifier_value>synthetic construct</INSDQualifier_value>
</INSDQualifier>
</INSDFeature_quals>
</INSDFeature>
</INSDSeq_feature-table>
<INSDSeq_sequence>atggg ttcctcttttctatcttccttctagcccttctctcttgcc tgaccgtgcccgcgtcagcctaccaagtacgcaactcctcgggcc tctaccacgtcaccaatgattgccctaactcgagtattgtgtacg agacggccgataccattctacactctccggggtgtgtcccttgcg ttcgcgagggtaacaactcgaggtgttgggtggcggtggcccca cagtcgccaccagggacggcaaactccccacaacgcagcttcgac
```

-continued

```
atcatatcgatctgcttgtcgggagcgccaccctttgctcggccc tctatgtggggacttgtgcgggtctgtctttcttgtcggccaac tgttcaccttctcccccagacgccactggacaacgcaagactgca actgctctatctaccccggccatataacgggtcaccgcatggcat gggatatgatgatgaactggtcccctacaacagcgctggtagtag cccagctgctcagggtcccgcaagccatcgtggatatgatcgccg gtgcccactggggagtcctagcgggcatagcgtatttctccatgg tagggaactgggcgaaggtcctggtagtgctgttgctgttcgccg gcgtcgatgccaacaccttcaccactggggggagtgctgccagga ccacgaccggactcgtcagtcttttcagtccgggcgccaagcaga atatccagctgatgaacaccaacggcagttggcacatcaatcgca cggccttgaactgtaatgcgagcctcgacaccggctgggtggggg gctcttctaccaccacaaattcaactcctcgggctgccccgagag gatggccagctgtaaacccttgccgattttgaccagggctgggg ccctatcacctacgccaacggaagcggccctgaacaccgcccta ctgctggcactacccccaaagccctgtggtgtcgtgtcagcgaa gaccgtgtgtggcccagtgtattgtttcactcctagccccgtggt ggtgggaacgaccaacgtgctgggcgaccctacctacggctgggg tgacaatgatacggacgtcctcatccttaataacaccaggccacc gttgggcaattggttcggttgcacctggatgaactcatctggatt taccaaagtgtgcggagcgcctccttgcgtcatcggaggagtggg caacaacaccttgcactgccccactgactgtttccgcaagcatcc agaagccacatactctcggtgtggctccggtccctggatcacgcc caggtgcctggtccactatccttataggctttggcattacccttg caccgtcaactacaccatgttcaaggtcaggatgtacgtgggagg ggtcgagcacaggctggaagctgcttgcaactggacgcgaggcga gcgttgtgatctggacgacagggacaggtccgagctcagcccgct gctgctgtccaccacacagtggcaggtccttccgtgctccttcac gaccttaccagccttgaccaccggcctcatccacctccaccggaa catcgtggacgtgcaatatttgtacgggggggggtcaagcattgtg tcctgggccatcaagtgggaatacgtcatcctcttgtttctcctg cttgcagacgcgcgcatctgctcctgcttgtggatgatgttactc
``` atatcccaagcggaggcgtaa</INSDSeq_sequence>
</INSDSeq>
</SequenceData>
</ST26SequenceListing>

---

What is claimed is:

1. A method for preparing an immunogenic composition comprising a viral antigen of hepatitis C virus (HCV), which comprises: (a) providing HCV pseudoparticles; (b) treating the HCV pseudoparticles with α2-3,6,8,9 neuraminidase A to remove sialic acids on the surfaces of the HCV pseudoparticles, and (c) isolating the HCV pseudoparticles produced in step (b) to generate the immunogenic composition.

2. The method of claim 1, wherein the HCV pseudoparticles have glycoproteins E1 and E2 of HCV.

3. The method of claim 1, wherein the HCV pseudoparticles are treated with α2-3,6,8,9 neuraminidase A for 0.5 to 4 hr in the step (b).

4. The method of claim 1, which further comprises a step (d), comprising mixing the HCV pseudoparticles of the step (c) with a pharmaceutically acceptable carrier to generate the immunogenic composition.

* * * * *

SEQUENCE LISTING

Sequence total quantity: 1
SEQ ID NO: 1          moltype = DNA  length = 1734
FEATURE               Location/Qualifiers
source                1..1734
                      mol_type = other DNA -continued

```
                    organism = synthetic construct
SEQUENCE: 1
atgggttcct ctttttctat cttccttcta gcccttctct cttgcctgac cgtgcccgcg   60
tcagcctacc aagtacgcaa ctcctcgggc ctctaccacg tcaccaatga ttgccctaac  120
tcgagtattg tgtacgagac ggccgatacc attctacact ctccggggtg tgtcccttgc  180
gttcgcgagg gtaacaactc gaggtgttgg gtggcggtgg cccccacagt cgccaccagg  240
gacggcaaac tccccacaac gcagcttcga catcatatcg atctgcttgt cgggagcgcc  300
acccttttgct cggccctcta tgtgggggac ttgtgcgggt ctgtctttct tgtcggccaa  360
ctgttcacct tctcccccag acgccactgg acaacgcaag actgcaactg ctctatctac  420
cccggccata taacgggtca ccgcatggca tgggatatga tgatgaactg gtcccctaca  480
acagcgctgg tagtagccca gctgctcagg gtcccgcaag ccatcgtgga tatgatcgcc  540
ggtgcccact ggggagtcct agcgggcata gcgtatttct ccatggtagg gaactgggcg  600
aaggtcctgg tagtgctgtt gctgttcgcc ggcgtcgatg ccaacacctt caccactggg  660
gggagtgctg ccaggaccac gaccggactc gtcagtcttt tcagtccggg cgccaagcag  720
aatatccagc tgatgaacac caacggcagt tggcacatca atcgcacggc cttgaactgt  780
aatgcgagcc tcgacaccgg ctgggtggcg gggctcttct accaccacaa attcaactcc  840
tcgggctgcc ccgagaggat ggccagctgt aaaccccttg ccgattttga ccagggctgg  900
ggccctatca cctacgccaa cggaagcggc cctgaacacc gcccctactg ctggcactac  960
cccccaaagc cctgtggtgt cgtgtcagcg aagaccgtgt gtggcccagt gtattgtttc 1020
actcctagcc ccgtggtggt gggaacgacc aacgtgctgg gcgaccctac ctacggctgg 1080
ggtgacaatg atacggacgt cctcatcctt aataacacca ggccaccgtt gggcaattgg 1140
ttcggttgca cctggatgaa ctcatctgga tttaccaaag tgtgcggagc gcctccttgc 1200
gtcatcggag gagtgggcaa caacaccttg cactgcccca ctgactgttt ccgcaagcat 1260
ccagaagcca catactctcg gtgtggctcc ggtccctgga tcacgcccag gtgcctggtc 1320
cactatcctt ataggctttg gcattaccct tgcaccgtca actacaccat gttcaaggtc 1380
aggatgtacg tgggaggggt cgagcacagg ctggaagctg cttgcaactg gacgcgaggc 1440
gagcgttgtg atctggacga cagggacagg tccgagctca gcccgctgct gctgtccacc 1500
acacagtggc aggtccttcc gtgctccttc acgaccttac cagccttgac caccggcctc 1560
atccacctcc accggaacat cgtggacgtg caatatttgt acggggtggg gtcaagcatt 1620
gtgtcctggg ccatcaagtg ggaatacgtc atcctcttgt ttctcctgct tgcagacgcg 1680
cgcatctgct cctgcttgtg gatgatgtta ctcatatccc aagcggaggc gtaa         1734
```